(12) United States Patent
Rodney

(10) Patent No.: US 7,509,998 B1
(45) Date of Patent: Mar. 31, 2009

(54) FORCED AIR AROMATIC BED WARMER/COOLER

(76) Inventor: James W Rodney, P.O. Box 3515, Grass Valley, CA (US) 95945

( * ) Notice: Subject to any disclaimer, the term of this patent is extended or adjusted under 35 U.S.C. 154(b) by 581 days.

(21) Appl. No.: 11/413,382

(22) Filed: Apr. 27, 2006

Related U.S. Application Data

(63) Continuation-in-part of application No. 10/387,673, filed on Mar. 12, 2003, now Pat. No. 7,036,575.

(60) Provisional application No. 60/365,438, filed on Mar. 19, 2002.

(51) Int. Cl.
*F25B 29/00* (2006.01)
*A47C 27/00* (2006.01)

(52) U.S. Cl. .................. 165/201; 165/267; 165/138; 5/423

(58) Field of Classification Search .............. 5/284, 5/423, 654, 655.3, 687, 710; 128/203.12; 165/200, 201, 247, 267, 268, 58, 59, 138
See application file for complete search history.

(56) References Cited

U.S. PATENT DOCUMENTS

| | | | | |
|---|---|---|---|---|
| 1,142,876 A | * | 6/1915 | Davis et al. .................. 5/284 |
| 2,259,712 A | * | 10/1941 | Sweetland ............... 219/217 |
| 2,461,432 A | * | 2/1949 | Mitchell .................... 5/423 |
| 2,560,349 A | * | 7/1951 | Inglis ..................... 219/217 |
| 2,695,413 A | * | 11/1954 | Maat ...................... 219/217 |
| 3,101,488 A | * | 8/1963 | Peebles .................... 5/423 |
| 3,230,556 A | * | 1/1966 | Shippee .................... 5/423 |
| 3,444,922 A | * | 5/1969 | Dingman ................... 165/247 |
| 3,713,182 A | * | 1/1973 | McNeal .................... 5/421 |
| 4,151,658 A | * | 5/1979 | Hibino et al. ............. 5/663 |
| 4,777,802 A | * | 10/1988 | Feher ....................... 5/423 |
| 4,867,230 A | * | 9/1989 | Voss ........................ 5/423 |
| 4,939,804 A | * | 7/1990 | Grant ....................... 5/423 |
| 4,984,316 A | * | 1/1991 | Simpson et al. ............ 5/423 |
| 5,300,100 A | * | 4/1994 | Hickle et al. .............. 5/423 |
| 5,730,120 A | * | 3/1998 | Yonkers, Jr. .............. 5/423 |

(Continued)

FOREIGN PATENT DOCUMENTS

FR      2 589 343     *   5/1987

(Continued)

*Primary Examiner*—Ljiljana (Lil) V Ciric
(74) *Attorney, Agent, or Firm*—Robert M Hunter PLLC

(57) ABSTRACT

An apparatus and method for modifying the temperature and aromatically conditioning the air and surfaces within a bed environment. In preferred embodiments, the invention is a self-contained, forced air bed warmer or bed warmer/cooler and aromatic infuser which pre-heats, pre-cools and infuses aromatic influences into the interior sheets and covers of a bed to provide a controlled micro-environment that facilitates relaxation into restful sleep on cold or hot nights. Preferred embodiments include an air conditioning section comprising a body portion and a handle portion, said air conditioning section having an exterior surface that is adapted to receive the edge of a bed cover between said body portion and said handle portion; a fan; a heat transfer element; a temperature sensor; a control circuit connected to said temperature sensor; a timer mounted within said air conditioning section; an elongated air delivery section having two ends with an air entrance at one end and a primary air exit at the other end and a means for introducing aromatic influences into the air moving through it.

14 Claims, 10 Drawing Sheets

U.S. PATENT DOCUMENTS

| | | | | |
|---|---|---|---|---|
| 5,842,286 A | * | 12/1998 | Cantor | 34/96 |
| 5,887,303 A | * | 3/1999 | Raith | 5/658 |
| 5,956,863 A | * | 9/1999 | Allen | 34/97 |
| 6,285,828 B1 | * | 9/2001 | Cafaro | 392/385 |
| 6,473,920 B2 | * | 11/2002 | Augustine et al. | 5/423 |
| 6,711,767 B2 | * | 3/2004 | Klamm | 5/423 |

FOREIGN PATENT DOCUMENTS

| | | | | |
|---|---|---|---|---|
| FR | 2 673 822 | * | 9/1992 |
| GB | 1 213 123 | * | 11/1970 |
| GB | 2 135 860 A | * | 9/1984 |
| GB | 2 192 118 A | * | 12/1987 |
| GB | 2 227 943 A | * | 8/1990 |

* cited by examiner

FORCED AIR AROMATIC BED WARMER/COOLER

CROSS-REFERENCE TO RELATED APPLICATIONS

This application is a continuation-in-part of U.S. patent application Ser. No. 10/387,673, filed Mar. 12, 2003, soon to issue as U.S. Pat. No. 7,036,575, which claims the benefit of U.S. Provisional Application No. 60/365,438, filed Mar. 19, 2002; the disclosures of which applications are incorporated by reference as if fully set forth herein.

STATEMENT REGARDING FEDERALLY SPONSORED RESEARCH OR DEVELOPMENT

Not Applicable

BACKGROUND OF THE INVENTION

This invention relates to bed warmers and bed coolers. In particular, the invention relates to bed warmers and bed coolers that heat or cool the interior of a bed via the use of a directed flow of warm air or cool air.

Bed warmers of various designs have been used for centuries to alleviate the discomfort of getting into a cold bed. More recently, devices have been created that both warm and cool the interior of a bed in an attempt to provide totally controlled temperature conditions within the bed.

The background art is characterized U.S. Pat. Nos. 1,142,876; 2,259,712; 2,461,432; 2,560,349; 2,695,413; 3,101,488; 3,230,556; 3,444,922; 3,713,182; 4,151,658; 4,777,802; 4,867,230; 4,939,804; 4,984,316; 5,300,100; 5,730,120; 5,842,286; 5,887,303; 5,956,863; 6,285,828; 6,473,920 and 6,711,767 the disclosures of which patents are incorporated by reference as if fully set forth herein. The background art is also characterized by United Kingdom Patent Nos. 1 213 123; GB 2 135 860 A; GB 2 192 118 A; and GB 2 227 943 A; and by France Patent Nos. 2 589 343; and 2 673 822.

Sweetland in U.S. Pat. No. 2,259,712 discloses a bed warmer with a thermostat for control of the temperature of the heating coil or heated air. This invention is limited in that no timer or heat/cold storage is provided. Moreover, the configuration of the unit is not such that the unit can be placed between the bottom sheet and bed cover with its handle overlapping the bed cover.

Inglis in U.S. Pat. No. 2,560,349 discloses an air conditioner for heating or cooling a bed. The device includes a thermostat for control of the temperature of the heated air. This invention is limited in that no timer or heat/cold storage is provided. Moreover, the configuration of the unit is not such that the unit can be placed between the bottom sheet and bed cover with its handle overlapping the bed cover.

Ter Mat is U.S. Pat. No. 2,695,413 discloses a ventilating device for beds. The device includes a thermostat for control of the temperature of the bed. This invention is limited in that no timer or heat/cold storage is provided. Moreover, the configuration of the unit is not such that the unit can be placed between the bottom sheet and bed cover with its handle overlapping the bed cover.

Another device, disclosed U.S. Pat. No. 3,230,556 issued to Shippee, discloses a construction for maintaining a controlled temperature environment in a bed. It consists of a shaped air distributing nozzle, a separate unit with a fan for inducing air flow, a heating means for increasing the temperature of the air and controls for the unit including a clock for timed control, a heat regulator and a fan switch. This invention is limited in that no heat/cold storage is provided. Moreover, the configuration of the unit is not such that the unit can be placed between the bottom sheet and bed cover with its handle overlapping the bed cover.

Another device, disclosed in U.S. Pat. No. 3,444,922 issued to Dingman, shows an apparatus for regulating the conditions of a bed by passing air about the occupant of the bed. The apparatus includes a distributor head connected to a separate cabinet containing an air pump, a temperature exchange chamber or plenum, a remote hand control box and may also include sensors to monitor temperature and humidity. This invention is limited in that no timer or heat/cold storage is provided. Moreover, the configuration of the unit is not such that the unit can be placed between the bottom sheet and bed cover with its handle overlapping the bed cover.

McNeal in U.S. Pat. No. 3,713,182 discloses a bedclothes elevator and bed warmer. This invention is limited in that no timer or heat/cold storage is provided. Moreover, the configuration of the unit is not such that the unit can be placed between the bottom sheet and bed cover with its handle overlapping the bed cover.

Hibino et al. in U.S. Pat. No. 4,151,658 disclose a bed clothes drying device. This invention is limited in that no heat/cold storage is provided. Moreover, the configuration of the unit is not such that the unit can be placed between the bottom sheet and bed cover with its handle overlapping the bed cover.

Yet another device, shown in U.S. Pat. No. 4,777,802 to Feher, describes a modified blanket assembly construction containing cavities or chambers through which warm or cool air is directed. Peltier effect elements are selectively energizable in a separate unit to heat or cool air provided to the blanket assembly cavities. This invention is limited in that no timer or heat/cold storage is provided. Moreover, the configuration of the unit is not such that the unit can be placed between the bottom sheet and bed cover with its handle overlapping the bed cover.

Voss in U.S. Pat. No. 4,867,230 disclose a convection blanket warmer. This invention is limited in that no timer or heat/cold storage is provided. Moreover, the configuration of the unit is not such that the unit can be placed between the bottom sheet and bed cover with its handle overlapping the bed cover.

Simpson et al. in U.S. Pat. No. 4,984,316 disclose a bed warmer that is used in conjunction with a hair drier. This invention is limited in that no timer or heat/cold storage is provided. Moreover, the configuration of the unit is not such that the unit can be placed between the bottom sheet and bed cover with its handle overlapping the bed cover.

Hickle et al. in U.S. Pat. No. 5,300,100 disclose a body warmer. This invention is limited in that no timer or heat/cold storage is provided. Moreover, the configuration of the unit is not such that the unit can be placed between the bottom sheet and bed cover with its handle overlapping the bed cover.

Cantor in U.S. Pat. No. 5,842,286 discloses a multi-functional hand-held hair drier that includes a barrel that discharges heated air in an axial direction and in two transverse directions. This invention is limited in that no thermostat, timer or heat/cold storage is provided. Moreover, the configuration of the unit is not such that the unit can be placed between the bottom sheet and bed cover with its handle overlapping the bed cover.

Raith in U.S. Pat. No. 5,887,303 discloses a bed warmer apparatus. This invention is limited in that no timer or heat storage is provided. Moreover, the configuration of the unit is not such that the unit can be placed between the bottom sheet and bed cover with its handle overlapping the bed cover.

Allen in U.S. Pat. No. 5,956,863 discloses a hair dryer apparatus and method. This invention is limited in that no thermostat, timer or heat/cold storage is provided. Moreover, the configuration of the unit is not such that the unit can be placed between the bottom sheet and bed cover with its handle overlapping the bed cover.

Cafaro in U.S. Pat. No. 6,285,828 discloses an infrared hair dryer heater. This invention is limited in that no timer or heat/cold storage is provided. Moreover, the configuration of the unit is not such that the unit can be placed between the bottom sheet and bed cover with its handle overlapping the bed cover.

Foster et al. in United Kingdom Patent No. 1 213 123 disclose a blanket for effecting heating and cooling of beds. This invention is limited in that no thermostat, timer or heat/cold storage is provided. Moreover, the configuration of the unit is not such that the unit can be placed between the bottom sheet and bed cover with its handle overlapping the bed cover.

Matossian et al. in United Kingdom Patent No. GB 2 135 860 A disclose an electric bed warmer. This invention is limited in that no air movement means is provided. Moreover, the configuration of the unit is not such that the unit can be placed between the bottom sheet and bed cover with its handle overlapping the bed cover.

Mappelback et al. in United Kingdom Patent No. GB 2 192 118 A disclose a liquid-filled bed warmer. This invention is limited in that no air movement means is provided. Moreover, the configuration of the unit is not such that the unit can be placed between the bottom sheet and bed cover with its handle overlapping the bed cover.

Simpson et al. in United Kingdom Patent No. GB 2 227 943 A disclose bed warmer. The disclosure of this patent is substantially the same at that of U.S. Pat. No. 4,984,316, described above.

Girard in France Patent No. FR2589343 discloses bed drying device. This invention is limited in that the configuration of the unit is not such that the unit can be placed between the bottom sheet and bed cover with its handle overlapping the bed cover.

Georges in France Patent No. FR2673822 discloses a bed warmer. This invention is limited in that the configuration of the unit is not such that the unit can be placed between the bottom sheet and bed cover with its handle overlapping the bed cover.

While background art devices may achieve the basic objective of controlling the air temperature within the bed, they share several disadvantages. First, they have multiple parts that, in order to function properly, may need to be assembled in somewhat complex configurations and to be precisely adjusted, which can make setting up the devices cumbersome and time consuming. Second, some of these devices contain or are inter-connected by electrical wires that rest in close proximity to the bed occupant during sleep, creating the possibility of shock or even electrocution. Third, in most cases, use of these devices requires that the bed coverings be removed, the device assembled and installed and the bed re-made. This makes them complicated and inconvenient to use, especially in the circumstance where a single device is to be used with multiple beds. Fourth, these devices are designed for continuous operation during the sleep cycle. It has been shown that the best conditions for sleep include absolute quiet and stillness. In addition, the healthiest state for the sleeping body has been demonstrated to be one in which the body is allowed to maintain it own optimal temperature via homeostasis, as opposed to continuously adjusting to imposed material or moving air temperatures. Thus, conditions may be created by these devices that are actually energetically stressful and counter to relaxing sleep, such as noise, vibration, excessive heat and air disturbance around or across the body.

What is needed is an apparatus and method for modifying the temperature of bedding that is convenient to use and that does not induce stress in its user. What is also needed is an apparatus that is easily moved and repositioned and that can be used with multiple beds. What is also needed is an apparatus that is capable of inflating a bed by filling the space between the bottom sheet and covers with a small volume of hot air, creating a microenvironment that contributes to the user's sensation of comfort and deep relaxation.

BRIEF SUMMARY OF THE INVENTION

The present invention recognizes and addresses particular disadvantages of prior art principles and constructions. Accordingly, it is an object of the present invention to provide enhanced and highly efficient warming and/or cooling of a bed environment. It is an object of this invention to provide a simple way to obviate the need for cumbersome warming/cooling envelopes, hoses, tubes, blankets or dangerous electrical wires in or over the bed, by operating as a single easily movable unit without additional separate external attachments. It is a further object of this invention to allow the user to maintain the comfortable, familiar bed coverings to which they are accustomed. By modifying the temperature of those coverings themselves as well as the air envelope created inside them, the total bed environment is made immediately comfortable to the user. It is a further object of this invention to easily create pre-heated or pre-cooled microenvironments within multiple undisturbed beds, without removal or disturbance of bed linens or coverings. It is also an object of this invention to introduce temperature-conditioned air into the bed by simply forcing the air into the space between the bed linens (e.g., between the bottom sheet and the bed covers). When activated, the pressure of the entering air causes the bed covers themselves to inflate slightly, thereby automatically distributing the warmed or cooled air to all parts of the bed. Another object of preferred embodiment of this invention is to complete an operational cycle and bring the bed interior to a comfortable temperature, before the occupant enters the bed. After the device is removed, the resting body, with suitable insulating or air permeable coverings, then effortlessly maintains a comfortable temperature through the principle of homeostasis. This allows optimal conditions of silence and stillness to be maintained during the sleep phase, thereby enabling and facilitating deep relaxation and restful sleep. Yet another object of preferred embodiments of this invention is to provide air delivery means, comprised of a thermal mass material that retains the heat or cold supplied during activation, which may then be detached from the heating/cooling section. Preferably, the air delivery means then remains in the bed with the occupant and is placed near or against the body to provide additional passive warmth or cooling via thermal radiation and direct body contact. Yet another object of preferred embodiments of this invention is to create a microenvironment within the bed that makes possible the maintenance of lower ambient-air temperatures in the bedroom, thereby conserving energy and lessening the desiccating effects of dry and overheated air during sleep. Another object of preferred embodiments of this invention is to provide air delivery means, in the form of a stuffed animal, toy or other object which may be utilized after the operating cycle is completed as a detachable child's toy or novelty object. Preferably, the child's toy or novelty object contains thermal mass material which enables it to retain warmth or cold, thereby providing a safe and comforting object for the bed occupant to place against his or her body as a further aid to relaxation and sound sleep. It is also an object of preferred embodiments of this invention to introduce aromatic, herbal-conditioned air into the bed as an additional factor conducive to relaxation and restful sleep. It is also an object of preferred embodiments of this invention to utilize a twenty-four hour digital timer to allow the device to be set up beforehand at any hour of the day, and thereby to automatically activate and run through a timed operational cycle at the hour that the user has selected.

In a preferred embodiment, the invention is a device (Warm•Wand™) for modifying the temperature of bedding (e.g., a bottom sheet and a bed cover), said device comprising: a housing having an exterior and an interior, said housing defining an air intake, an air plenum and an air outlet; a fan (or other air moving device) mounted in said housing for moving air in said air intake, through said plenum and out said air outlet; a heat transfer element mounted within said housing for modifying the temperature of the air entering said air intake (e.g., conditioning the air); a temperature sensor mounted in said plenum for sensing the temperature of the air moving through said plenum; a control circuit connected to said temperature sensor, said control circuit being operative to maintain the temperature of air moving through said plenum at or below a selected temperature (e.g., acting as a thermostat); a timer mounted within (or on) said housing, said timer being operative to activate said fan and heat transfer element upon being turned on by means of a timer dial mounted on the exterior of said housing and to deactivate said fan and heat transfer element after a selected amount of time; and an elongated air delivery section having two ends and defining an air entrance at one end, a primary air exit at the other end and a plurality of secondary air exits adjacent to the other end, said air entrance being adapted to connect to said air outlet; wherein said elongated air delivery section has a longitudinal axis and comprises a flattened portion; wherein said primary air exit is situated at the terminus of said flattened portion and is adapted to discharge air substantially parallel to said longitudinal axis and far enough beneath a bed cover to cause the bedding to inflate; and wherein said plurality of secondary air exits are situated within said flattened portion and are adapted to discharge air substantially perpendicular to said longitudinal axis. Preferably, the device further comprises a handle attached to said housing. Preferably, handle is attached to the top rear of said housing and is forward projecting (e.g., projecting toward the air outlet and rendering the device U-shaped). Preferably, the heat transfer device is a heating element (e.g., a resistance coil). Preferably, the housing also defines a rear-facing air exhaust, said heat transfer device is a thermoelectric module that is adapted to heat and cool the air entering said air intake and said device further comprises a switch for switching the device between heating and cooling the air discharged from the device. Preferably, the device further comprises a power cord for supplying power to the device. Preferably, the elongated air delivery section is attachable to and detachable from said housing by means of a bayonet joint there between. Preferably, the outside of said air delivery section is configured to resemble an animal, toy or other object. Preferably, the air exit is the mouth of the animal or opening on the front of the toy or object. Preferably, the selected amount of time is variable between about one minute and about five minutes.

In another preferred embodiment, the invention is a device for modifying the temperature of bedding, said device comprising: a housing having an exterior and an interior, said housing defining an air intake, an air plenum and an air outlet; a fan mounted in said housing for moving air in said air intake, through said plenum and out said air outlet; a heat transfer element mounted within said housing for modifying the temperature of the air entering said air intake; a temperature sensor mounted in said plenum for sensing the temperature of the air moving through said plenum; a control circuit connected to said temperature sensor, said control circuit being operative to maintain the temperature of air moving through said plenum at or below a selected temperature; a timer mounted within said housing, said timer being operative to activate said fan and heat transfer element upon being turned on by means of a timer dial mounted on the exterior of said housing and to deactivate said fan and heat transfer element after a selected amount of time; and an elongated, detachable air delivery section having two ends and defining an air entrance at one end and a primary air exit at the other end, said air entrance being adapted to connect to said air outlet, said elongated air delivery section comprising a thermal gel medium having at least one air channel there through, said air channel connecting said air entrance and said air exit.

Yet another preferred embodiment of the invention is a device for modifying the temperature of bedding, said device comprising: a housing having an exterior and an interior, said housing defining an air intake, an air plenum and an air outlet; a fan mounted in said housing for moving air in said air intake, through said plenum and out said air outlet; a heat transfer element mounted within said housing for modifying the temperature of the air entering said air intake; a temperature sensor mounted in said plenum for sensing the temperature of the air moving through said plenum; a control circuit connected to said temperature sensor, said control circuit being operative to maintain the temperature of air moving through said plenum at or below a selected temperature; a timer mounted within said housing, said timer being operative to activate said fan and heat transfer element upon being turned on by means of a timer dial mounted on the exterior of said housing and to deactivate said fan and heat transfer element after a selected amount of time; and an elongated, detachable air delivery section having two ends and defining an air entrance at one end and a primary air exit at the other end, said air entrance being adapted to connect to said air outlet, said elongated air delivery section comprising a thermal gel medium having a plurality of air channels there through, said air channels connecting said air entrance and said air exit. Preferably, the housing also defines a rear-facing air exhaust, said heat transfer device is a thermoelectric module that is adapted to heat and cool the air entering said air intake and said device further comprises a switch for switching the device between heating and cooling the air discharged from the device. Preferably, the elongated air delivery section is attachable to and detachable from said housing by means of a bayonet joint there between, said bayonet joint comprising a plurality of lugs. Preferably, the paths of said air channels are tortuous.

In a further preferred embodiment, the invention is a device for modifying the temperature of bedding, said bedding comprising a bottom sheet and a cover, said device comprising: an air conditioning section having an exterior and an interior having an insulating liner, said air conditioning section defining an air intake, an air plenum and an air outlet and having a U-shaped slot that is adapted to receive an edge of said cover; a fan mounted in said air conditioning section for moving air in said air intake, through said plenum and out said air outlet; a heat transfer element mounted within said air conditioning section for modifying the temperature of the air entering said air intake; a temperature sensor mounted on said heat transfer element for sensing its temperature; a control circuit connected to said temperature sensor, said control circuit being operative to maintain the temperature of the heat transfer element at or below a selected temperature; a timer mounted within said air conditioning section, said timer being operative to activate said fan and heat transfer element upon being turned on by means of a timer dial mounted on the exterior of said air conditioning section and to deactivate said fan and heat transfer element after a selected amount of time; and an elongated air delivery section having two ends and defining an air entrance at one end, a primary air exit at the other end and a plurality of secondary air exits adjacent to the other end, said air entrance being adapted to connect to said air outlet.

In another preferred embodiment, the invention is a device for modifying the temperature of bedding, said bedding comprising a bottom sheet and a cover, said device comprising: an air conditioning section comprising a body portion and a handle portion, said an air conditioning section having an exterior surface that is adapted to receive an edge of said cover between said body portion and said handle portion and an interior surface defining an air intake, an air plenum and an air outlet; a fan mounted in said air conditioning section for moving air in said air intake, through said plenum and out said air outlet; a heat transfer element mounted within said air conditioning section for modifying the temperature of the air entering said air intake; a temperature sensor mounted on said heat transfer element for sensing its temperature; a control circuit connected to said temperature sensor, said control circuit being operative to maintain the temperature of the heat transfer element at or below a selected temperature; a timer mounted within said air conditioning section, said timer being operative to activate said fan and heat transfer element upon being turned on by means of a timer dial mounted on the exterior of said air conditioning section and to deactivate said fan and heat transfer element after a selected amount of time; and an elongated air delivery section having two ends with an air entrance at one end and a primary air exit at the other end, said air entrance being adapted to connect to said air outlet. In a preferred embodiment the device further comprises a plurality of secondary air exits adjacent to the other end.

In another preferred embodiment, the invention is a device for modifying the temperature of bedding, said device comprising: housing means having an exterior and an interior having an insulating liner, said housing means defining an air intake, an air plenum and an air outlet; means for moving air (e.g., a fan or blower) mounted in said housing, said means for moving air being operative to move air in said air intake, through said plenum and out said air outlet; means for heat transfer mounted within said housing means, said means for heat transfer being operative to modify the temperature of the air entering said air intake; means for temperature sensing mounted on said means for heat transfer, said means for temperature sending being operative to sense the temperature of the means for heat transfer; means for controlling connected to said means for temperature sensing, said means for controlling being operative to maintain the temperature of the means for heat transfer at or below a selected temperature; means for timing mounted within said housing means, said means for timing being operative to activate said means for moving air and said means for heat transfer upon being turned on by means of a timer dial mounted on the exterior of said housing means and to deactivate said means for moving air and said means for heat transfer after a selected amount of time; and means for air delivery, said means for air delivery being elongated, having two ends and defining an air entrance at one end, a primary air exit at the other end and a plurality of secondary air exits adjacent to the other end, said air entrance being adapted to connect to said air outlet.

In preferred embodiments, the invention is also a method. In a preferred embodiment, the invention is a method for modifying the temperature of bedding comprising a bottom sheet and a cover, said method comprising: placing a device disclosed herein within the bedding with said handle on top of the cover and said outlet below the cover; and setting the timer to cause the device to operate, thereby inflating the bedding. Preferably, the method further comprises detaching the air delivery section from the housing; leaving the air delivery section within the bedding; and removing the housing from the bedding.

In another preferred embodiment, the invention is a method for modifying the temperature of bedding comprising a bottom sheet and a cover having an edge, said method comprising: a step for placing a device of disclosed herein within the bedding with the edge of the cover being disposed in said U-shaped slot and said outlet being disposed below the cover; and a step for setting the timer to cause the device to operate. Preferably, the method further comprises: a step for detaching the air delivery section from the housing; a step for leaving the air delivery section within the bedding; and a step for removing the housing from the bedding.

In a preferred embodiment, the invention is an apparatus for modifying the temperature of bedding, said apparatus comprising: an air conditioning section comprising a housing having an air intake and an air exit, an air conditioning element, a fan, a thermostat and a timer; and a air delivery section having an air entrance that is attachable to and detachable from said air exit, said air delivery section comprising an elongated neck portion and a air diffuser portion; wherein said housing comprises a body and a handle with a slot there between that is adapted to support the edge of a bedcover and prevent its covering of said air intake; and wherein said elongated neck portion is adapted to position said diffuser sufficiently distant from said edge so that inflation of the bedding occurs upon activation of the fan.

Another preferred embodiment of the invention is a device for warming or cooling a bed, the device comprising: a (rear) housing, defining an air intake, interior air plenums and one or more air exits; a fan or other means for moving air into said air intake, through said air plenums and out said air exits; a heating element that functions to increase the temperature of the air that has entered said air intake; a temperature sensor attached to said heating element that monitors the temperature of said element; self-regulating safety temperature circuitry connected to said temperature sensor that automatically adjusts said heating element such that said heating element and/or the heated air remains below a specific safety temperature; a timer that can be set for a cycle such that said timer activates said device for a specified number of minutes or seconds and automatically deactivates said device when said timer has completed said cycle; an air delivery section, being one of said two connected sections of said device, serving as a means for moving air directionally forward and out said air exits. Preferably, said heating element is a thermoelectric heating/cooling element that either increases or decreases the temperature of the air that has entered said air intake, depending on the setting of a switch that reverses the polarity of said thermoelectric element. Preferably, the interior of said housing is divided into a plenum that directs conditioned air toward the front exits and a plenum that directs exhaust air toward the rear of said device. Preferably, the (front) air delivery section is partly comprised of a thermal mass substance, and may be detached after operation of said device and retained in the bed to provide additional heating. Preferably, the front air delivery section is in the form of a child's toy containing thermal mass material, and may be detached after operation of said device and left with a child to sleep with to provide an additional level of comfort.

In another preferred embodiment, the invention is a self-contained, forced air bed warmer or bed warmer/cooler which safely and efficiently pre-heats or pre-cools the interior sheets and covers of a bed to provide a comfortable micro-environment that facilitates relaxation into restful sleep on cold or hot nights. Preferred embodiments comprise a heating/cooling element section and an air delivery section that lock together via a bayonet type joint. Preferably, the heating/cooling element section is generally cylindrical with a handle connected at a single point at the top rear of the section and projecting forward. This handle preferably provides a means of easily manipulating the device as well as acts as a catch to prevent blankets or covers from sliding over the rear body/air intake and blocking the flow of air. In preferred embodiments, a portion of the handle also functions as an exit for a reverse air plenum in the heating/cooling version. The heating/cooling section preferably contains a high-efficiency fan or device for moving air and an element for heating or cooling air. These parts function together to create a flow of hot or cool air that travels through the housing and out the openings in the air delivery section. The air delivery sections preferably generally resemble a flattened and flared tube, a flat semi-flexible oval or a child's stuffed toy animal. The flat oval air delivery section is preferably comprised of a semi-flexible thermal gel that acts as a thermal mass to retain heat or cold from the conditioned air directed through it. This air delivery section is designed to be detached from the heating/cooing section after deactivation of the device, and to remain in the bed with the occupant to provide additional passive radiant and conductive warming or cooling. The child's toy air delivery section is preferably constructed with an internal layer of thermal gel that similarly retains heat and cold. The child's toy air delivery section may also be detached from the heating/cooling section after deactivation and left with the child to sleep with to provide an additional level of comfort as a further aid to sound sleep. Auxiliary holes are preferably provided in the air delivery section to allow a wider distribution of the air exiting the device and provide an alternative airflow in the event that the primary exit becomes obstructed. Preferred embodiments of the device comprise a timer mechanism that can be set such that the device activates for a period of one to five minutes and then automatically deactivates. Preferably, the device also contains a thermal sensor and self-regulating safety temperature circuitry that automatically adjusts the heating/cooling element and/or the heated air (when in the heating mode) such that they remain below a specific safety temperature regardless of the amount of air flowing through the device.

In a preferred embodiment, the invention is a self-contained forced air bed warmer or bed warmer/cooler which safely and efficiently pre-heats or pre-cools the interior sheets and covers of a bed to provide a comfortable micro-environment that will facilitate relaxation into restful sleep on cold or hot nights. Preferably, it is an easily moveable, self-contained, hand-held appliance constructed of lightweight injection molded plastic.

In preferred embodiments, the design and position of the handle of the device maintain the device in an optimal position relative to the bed covers and for unimpeded airflow. If one attempted to use a background art device for this purpose, it would not stay in position and the covers would invariably block the air intake, causing overheating, possible fire hazard and electrical cutoff or possible short circuit. Preferred embodiments of the device have an insulated air delivery section that is of sufficient length to conduct the warmed air into the mid-section of the bed. Background art devices do not have the length to perform this function and so would conduct very little air into the bed interior. In preferred embodiment, the air delivery section is a progressively flattened, flared and perforated tube, and represents an optimal shape for slipping between bed covers. Background art devices maintain near cylindrical profiles and would be ineffective for this purpose. Preferably, the device has a manual set minute timer and automatic safety temperature control circuitry that allows the device to be activated and left to safely complete the heating cycle unattended. Background art devices have no such features and thus are unsafe for this purpose.

In a preferred embodiment, the invention is a self-contained forced air bed warmer that comprises means wherein elements such as aromatic herbal packets may be suspended in or introduced into the air moving through the device such that the air is modified or further conditioned by those elements, thereby adding aromatic or olfactory influences that further facilitate relaxation into restful sleep.

Preferred embodiments of the device further comprise a twenty-four hour digital timer mechanism that can be set such that the device activates either immediately or automatically at any specified time within a twenty-four hour period for a period up to ten minutes and then automatically deactivates. Setting of the timer is preferably easily done via pushbuttons located on the exterior of the device housing.

In a preferred embodiment, the invention is a device for modifying the temperature of bedding comprising a bed cover, said device comprising: a housing having an exterior and an interior, said housing defining an air intake, an air plenum and an air outlet; a fan mounted in said housing for moving air in said air intake, through said plenum and out said air outlet; a heat transfer element mounted within said housing for modifying the temperature of the air entering said air intake; a temperature sensor mounted in said plenum for sensing the temperature of the air moving through said plenum; a control circuit connected to said temperature sensor, said control circuit being operative to maintain the temperature of air moving through said plenum at or below a selected temperature; a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and an elongated air delivery section having two ends and defining an air entrance at one end, a primary air exit at the other end and a plurality of secondary air exits adjacent to the other end, said air entrance being adapted to connect to said air outlet; wherein said elongated air delivery section has a longitudinal axis and comprises a flattened portion; wherein said elongated air delivery section comprises means for suspending an aromatic element in and introducing an aromatic substance into the air moving through said elongated air delivery section such that said air is modified or further conditioned by said elements; wherein said primary air exit is situated at the terminus of said flattened portion and is adapted to discharge air substantially parallel to said longitudinal axis and far enough beneath a bed cover to cause the bedding to inflate; and wherein said plurality of secondary air exits are situated within said flattened portion and are adapted to discharge air substantially perpendicular to said longitudinal axis.

In a further preferred embodiment, the invention is a device for modifying the temperature of bedding, said bedding comprising a bottom sheet and a cover, said device comprising: an air conditioning section having an exterior and an interior having an insulating liner, said air conditioning section defining an air intake, an air plenum and an air outlet and having a U-shaped slot that is adapted to receive an edge of said cover; a fan mounted in said air conditioning section for moving air in said air intake, through said plenum and out said air outlet; a heat transfer element mounted within said air conditioning section for modifying the temperature of the air entering said air intake; a temperature sensor mounted on said heat transfer element for sensing its temperature; a control circuit connected to said temperature sensor, said control circuit being operative to maintain the temperature of the heat transfer element at or below a selected temperature; a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and an elongated air delivery section having two ends and defining an air entrance at one end, a primary air exit at the other end and a plurality of secondary air exits adjacent to the other end, said air entrance being adapted to connect to said air outlet.

In yet another preferred embodiment, the invention is a device for modifying the temperature of bedding, said bedding comprising a bottom sheet and a cover, said device comprising: an air conditioning section comprising a body portion and a handle portion, said an air conditioning section having an exterior surface that is adapted to receive an edge of said cover between said body portion and said handle portion and having an interior surface defining an air intake, an air plenum and an air outlet; a fan mounted in said air conditioning section for moving air in said air intake, through plenum and out said air outlet; a heat transfer element mounted within said air conditioning section for modifying the temperature of the air entering said air intake; a temperature sensor mounted on said heat transfer element for sensing its temperature; a control circuit connected to said temperature sensor, said control circuit being operative to maintain the temperature of the heat transfer element at or below a selected temperature; a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and an elongated air delivery section having two ends with an air entrance at one end and a primary air exit at the other end, said air entrance being adapted to connect to said air outlet.

In another preferred embodiment, the invention is a device for modifying a bedding environment, said bedding comprising a bottom sheet and a cover, said device comprising: an air conditioning section comprising a body portion and a handle portion, said an air conditioning section having an exterior surface that is adapted to receive an edge of said cover between said body portion and said handle portion and having an interior surface defining an air intake, an air plenum and an air outlet; a fan mounted in said air conditioning section for moving air in said air intake, through said plenum and out said air outlet; a heat transfer element mounted within said air conditioning section for modifying the temperature of the air entering said air intake; a temperature sensor mounted on said heat transfer element for sensing its temperature; a control circuit connected to said temperature sensor, said control circuit being operative to maintain the temperature of the heat transfer element at or below a selected temperature; a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and an elongated air delivery section having two ends with an air entrance at one end and a primary air exit at the other end, said air entrance being adapted to connect to said air outlet; wherein said elongated air delivery section comprises means for introducing an aromatic substance into the air moving through said elongated air delivery section such that said air is modified or further conditioned.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate presently preferred embodiments of the invention. In the drawings.

Figure 1:
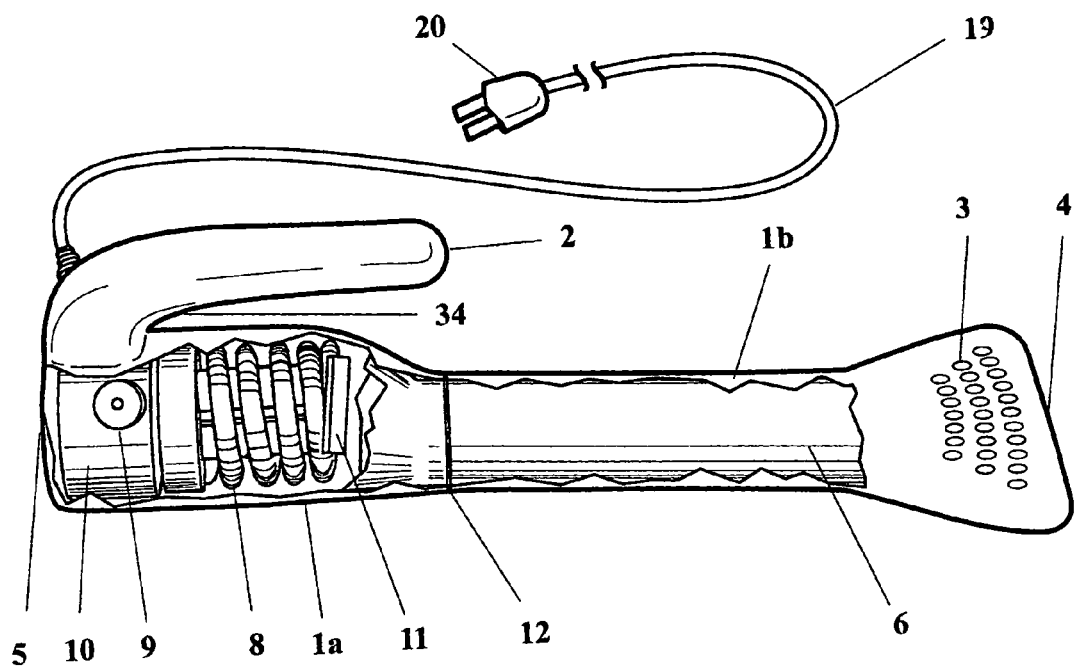
FIG. 1 is a right side perspective view of a device constructed in accordance the invention, designed to produce heating only, showing a cutaway view of the interior components, wherein the heating element section is attached to a basic air delivery section.

The following reference numerals are used to indicate the parts and environment of the invention on the drawings:
1a heating element section, heating/cooling element section, air conditioning section, housing, main body, body portion
1b basic air delivery section
1c stuffed toy air delivery section
1d thermal gel air delivery section
1e herbal infuser air delivery section
2 handle
3 secondary air exits
4 primary air exit
5 air intake, rear air intake
6 heat-resistant liner
8 heating coil, heat exchanger, heat transfer element
9 timer
9a external timer dial, timer dial
10 fan unit, fan, blower, other device for moving air
11 temperature sensor
12 bayonet type joint
13 bayonet lugs
14 lower heat transfer element
15 thermoelectric module, thermoelectric element
16 upper reverse air plenum
17 upper heat transfer element
18 reverse air exit, air exhaust
19 power cord
20 electrical plug
21 polarity switch
23 thermal gel medium
24 thermal gel air channels
25 stuffed toy covering
26 flexible, heat-resistant tube
30 bottom sheet
32 cover
34 slot, U-shaped slot
35 herbal infuser enclosure basket, internal enclosure, perforated herbal infuser enclosure
36 herbal infuser enclosure cover, infuser enclosure cover, enclosure door
37 herbal infuser basket perforations, enclosure perforations
38 herbal packet, shaped herbal packet
39 digital timer pushbuttons, exterior pushbuttons
40 digital timer unit
41 digital timer LCD panel, LCD panel

DETAILED DESCRIPTION OF THE INVENTION

Referring to FIG. 1, a preferred embodiment of the invention is presented. This embodiment is designed to produce heating only and preferably comprises two main sections: heating element section 1a and air delivery section 1b which lock together via bayonet type joint 12. Heating element section 1a is generally cylindrical, with air intake 5 on one (rear) end and forward-projecting handle 2 attached at the top rear. The front of elongated air delivery section 1b is flattened into a flare that terminates in primary air exit 4. Patterns of holes on the top and bottom of the front flare serve as secondary air exits 3, providing auxiliary air exits for the device or alternative exits in the event that primary exit 4 becomes obstructed. Both heating element section 1a and air delivery section 1b are preferably constructed of a plastic, more preferably an injection-molded thermoplastic.

Mounted inside heating element section 1a are the following: high efficiency fan or other device for moving air 10, heating coil 8 and temperature sensor 11. Temperature sensor 11 is used to monitor the temperature of heating coil 8 and/or the air heated by heating coil 8 and produces signals that are processed by a control circuit (not shown) that is operative to maintain the temperature of heating coil 8 and/or the air heated by heating coil 8 at or below a selected temperature (e.g., 100 F). A manual set timer 9 is preferably mounted on the right side of the casing of fan 10. Lining the entire inside of the plastic casing of both heating element section 1a and air delivery section 1b is heat-resistant insulating liner 6. Power cord 19 terminated in standard 120-volt wall plug 20 preferably connects to the device circuitry (not shown) through the left side of handle 2.

Figure 2:
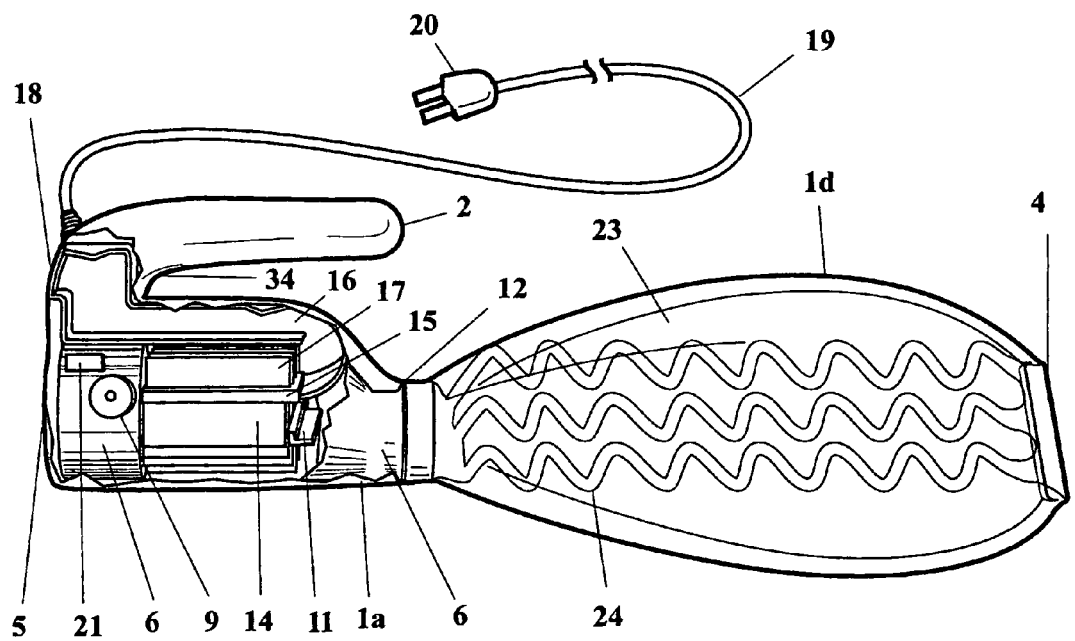
FIG. 2 is a right side perspective view of a device constructed in accordance the invention, designed to produce both heating and cooling, showing a cutaway view of the interior components, wherein the heating/cooling element section is attached to a thermal gel air delivery section.

Referring to FIG. 2, another preferred embodiment of the invention is presented. This embodiment is designed to produce both heating and cooling and comprises two main sections: heating/cooling element section 1a and thermal mass air delivery section 1d that lock together via bayonet type joint 12. Heating/cooling element section 1a is generally cylindrical with air intake 5 on one end and forward projecting handle 2 attached at the top rear. Air delivery section 1d generally defines a flattened oval composed of a semi-rigid thermal gel through which run a plurality of tortuous air passages 24 terminating at primary air exit 4.

Mounted inside heating/cooling element section 1a are the following: high efficiency fan or device for moving air 10, thermoelectric module 15, upper heat transfer element 17, lower heat transfer element 14 and temperature sensor 11. Manual timer dial 9 and polarity switch 14 are preferably mounted on the right side of the casing of fan 10. Heating/cooling element section 1a is divided into two separate chambers, one located above and one located below thermoelectric element 15. Top chamber 16 forms an airtight reverse air plenum that terminates at reverse air exit 18 in the back end of handle 2. Lining the inside of the preferably plastic casing of heating/cooling element section 1a is heat-resistant, insulating liner 6. Power cord 19 terminated in a standard 120 volt wall plug 20 is connected to the device circuitry (not shown), preferably through the left side of handle 2.

Figure 3:
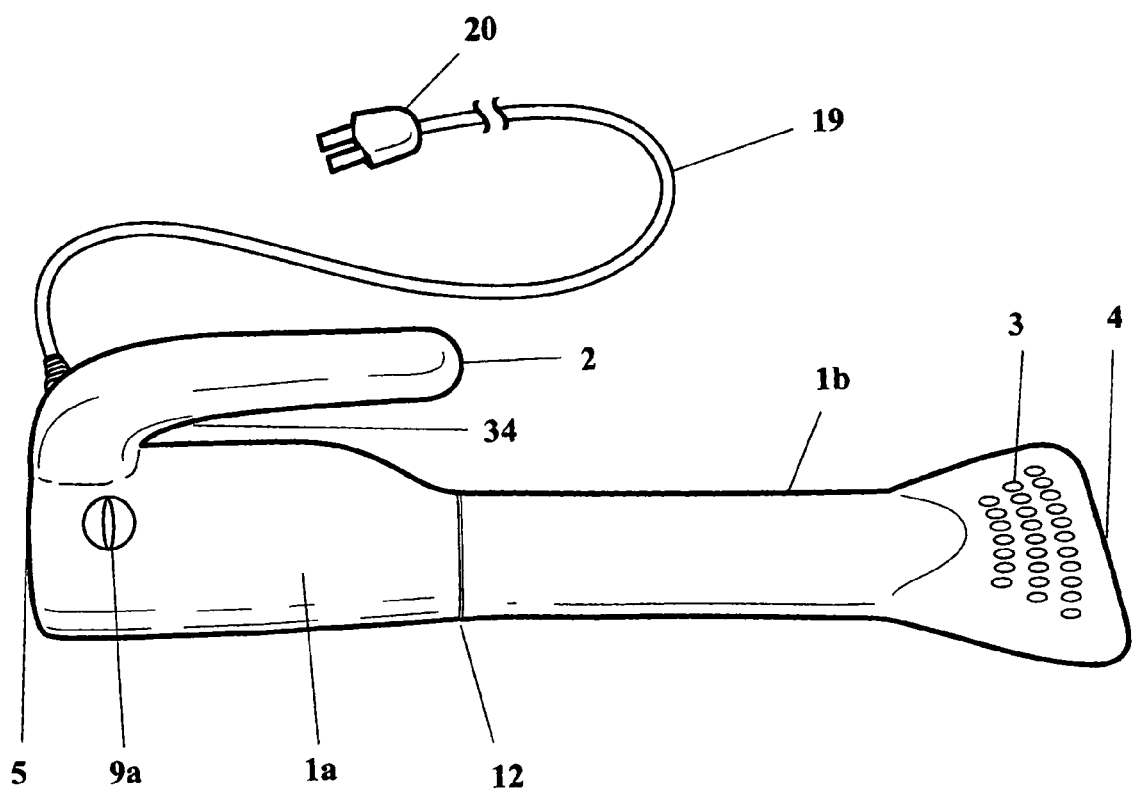
FIG. 3 is a right side perspective view of the device of FIG. 1, showing an exterior view wherein a heating element section is attached to a basic air delivery section.

Referring to FIG. 3 is an external right-side perspective view of the device of FIG. 1 is presented. This view shows basic air delivery section 1b with primary air exit 4 and secondary air exits 3 attached via bayonet type joint 12 to heating element section 1a. Dial 9a for setting the timer is preferably located on the outside of the right rear of heating/cooling element section 1a.

Figure 4:
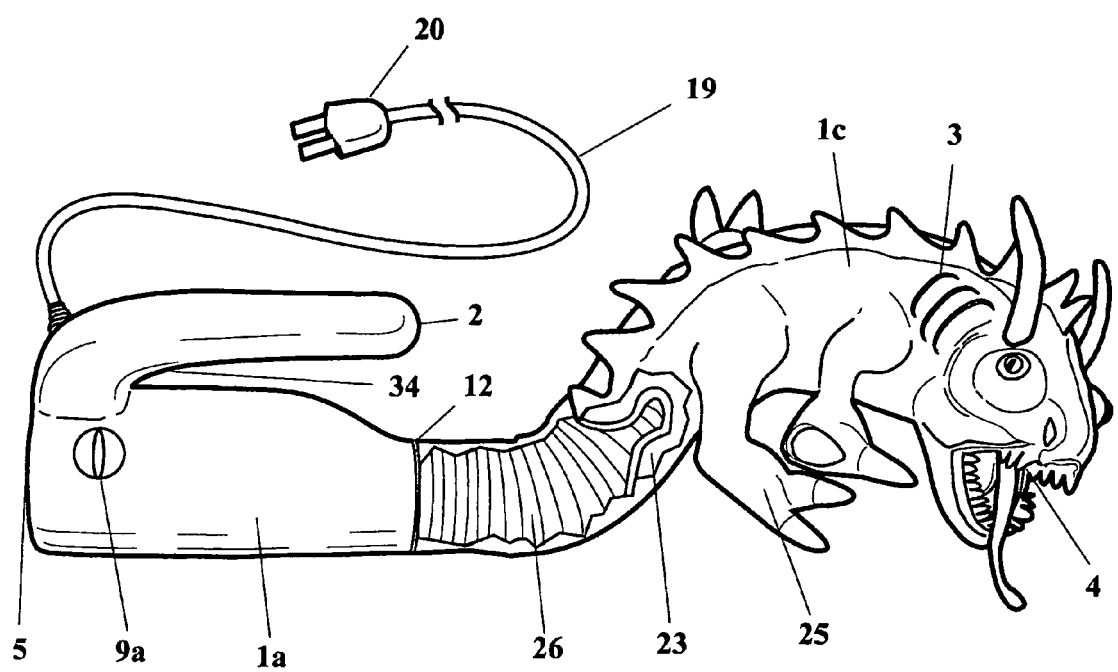
FIG. 4 is a right side perspective view of the device of FIG. 1, showing an exterior view wherein a heating element section is attached to a child's toy air delivery section, in which a cutaway view shows the interior construction of the toy air delivery section.

Referring to FIG. 4, an external right-side perspective view of the device of FIG. 1 is presented. This view shows child's stuffed toy air delivery section 1c attached to heating element section 1a. Stuffed toy air delivery section 1c consists of a flexible, heat-resistant tube 26 inside thermal mass covering 23. This assembly is then mounted inside a stuffed animal, toy or other object and terminates in primary air exit 4 at the toy's mouth or object's front opening and secondary air exits 3 at the toy's head or front of the object which preferably direct air rearward or to the sides. Bayonet type joint 12 locks the two sections 1a, 1c together. Dial 9a for setting the timer is preferably located on the outside of the right rear of heating element section 1a.

Examples of preferred objects include varieties of toys or stylized figurines other than animals such as cars, airplanes, boats, robots or unique cartoon characters. Preferably, these embodiments are constructed in a similar manner to the animal objects disclosed herein, e.g., with a layer of thermal mass material to retain heat. These embodiments are, in effect, functional stuffed toys, in that that they can be left on top of the bed with other conventional stuffed animals or toys. At bedtime, the object is simply attached for a short period of time to heating element section 1a to warm the bed and charge the object with heat. Then, the object is left in the bed for the child to sleep with. Varieties of these embodiments may be designed to meet the needs of slightly older children. These embodiments preferably include objects in the form of another type of soft toy, such a rocket ship, car, airplane, cartoon character, etc. or objects that are not considered toys, e.g., novelty items like a stuffed flower bouquet or a small stylized pillow.

Other examples of preferred objects include small firm pillows such as cylindrical or oval bolster pillows that may be covered with decorative prints and/or soft textured fabric like flannel cotton or acrylic pile. These embodiments are also preferably in a similar manner to the animal objects disclosed herein, e.g., with a layer of thermal mass material (e.g., gel pac) to retain heat. These embodiments preferably have semi flexible air channels running parallel to the longitudinal axis of the object, perhaps with a series of auxiliary tortuous air channels to facilitate thermal mass charging. The bayonet mount air entry opening and opposing air exit opening are preferably flush with the pillow ends such that they are not readily differentiated from the main body of the pillow. These embodiments can be left on top of the made bed as or with other decorative pillows. The object functions in a similar fashion to the stuffed toys and gel pac, i.e., at bedtime, it is attached to heating element section 1a which simultaneously warms the bed and charges the object with heat. The object is then be detached and used in the bed to be placed under the neck, lower back, etc. to provide comfort and relaxation to specific body areas.

Figure 5:
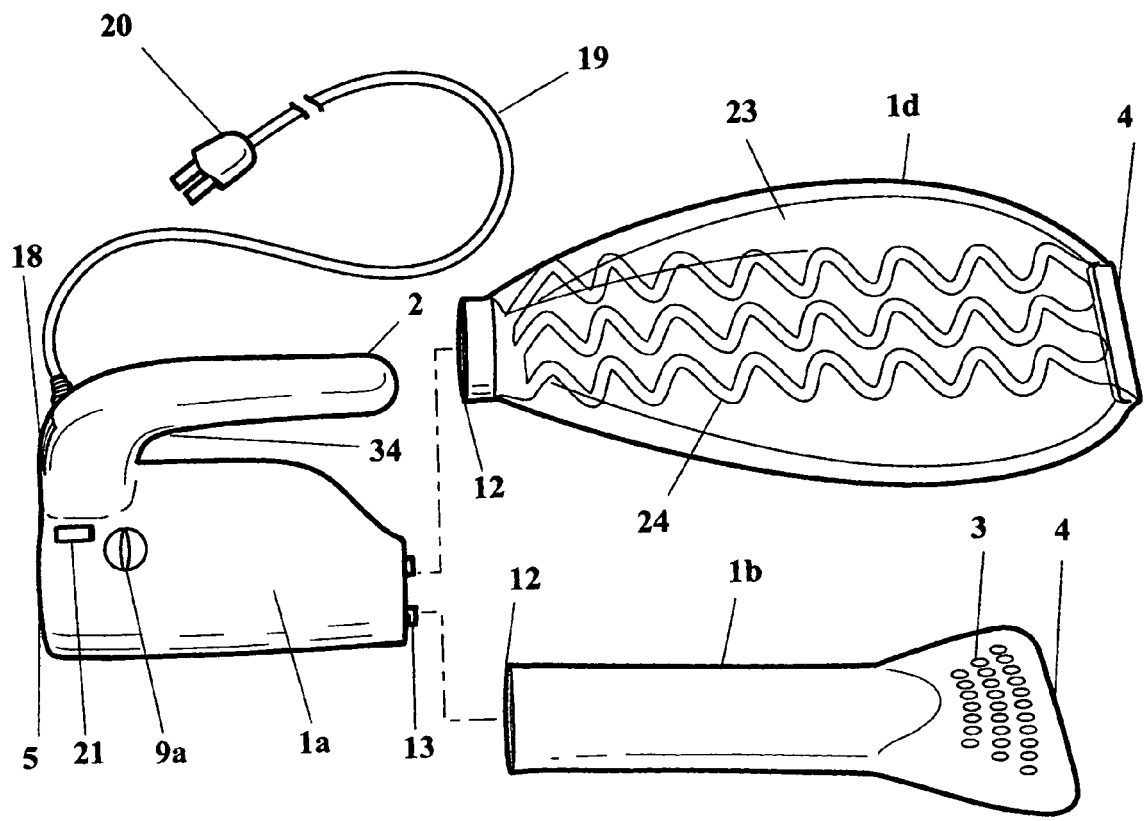
FIG. 5 is a right side perspective view of the device of FIG. 2 showing an exterior view of a heating/cooling element section separated from a thermal gel air delivery section and a basic air delivery section. Also shown are the bayonet lugs for the locking joint.

Referring to FIG. 5, a right side perspective view of the device of FIG. 2 is presented. This view shows an exterior view of heating element section 1aa detached from thermal gel air delivery section 1d and basic air delivery section 1b. The different air delivery sections are thus easily interchangeable via bayonet type joint 12, which utilizes lugs 13 to engage receptacles in air delivery sections 1b, 1d that lock heating element section 1aa to air delivery section 1b or air delivery section 1d.

Figure 6:
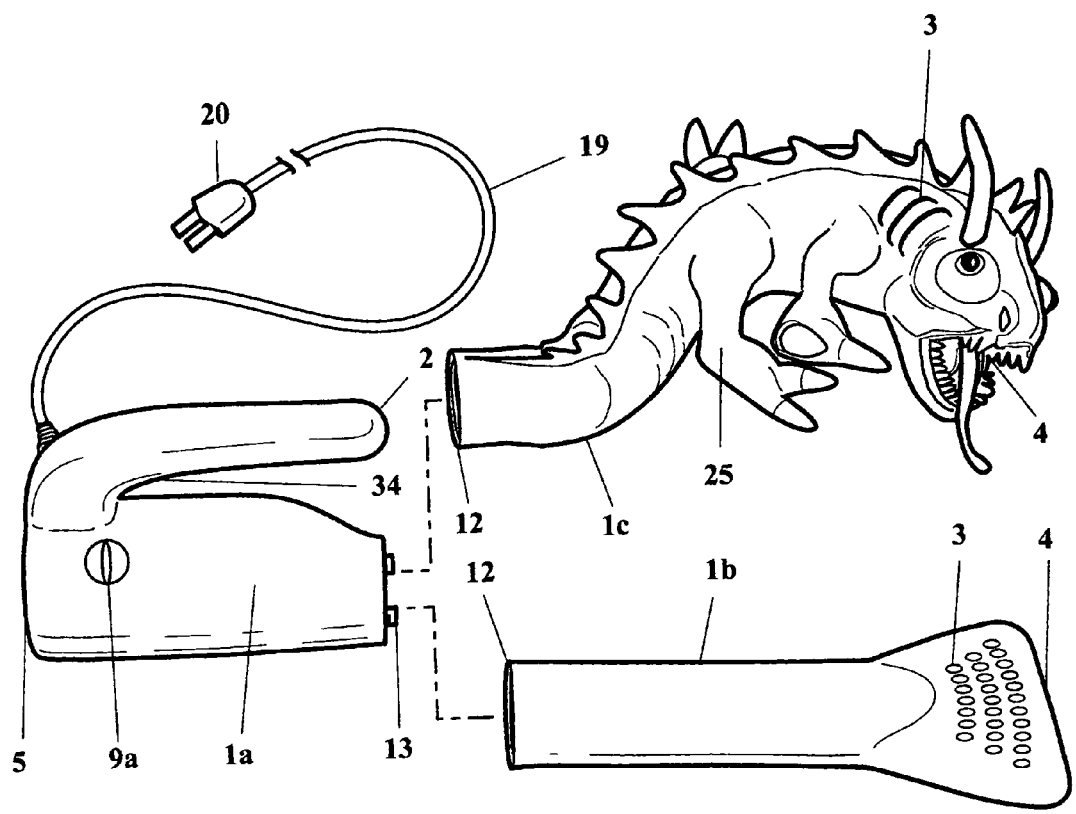
FIG. 6 is a right side perspective view of the device of FIG. 1 showing an exterior view of a heating element section separated from a child's toy air delivery section and a basic air delivery section. Also shown are the bayonet lugs for the locking joint.

Referring to FIG. 6, a right side perspective view of the device of FIG. 1 is presented, showing an exterior view of heating element section 1a detached from child's toy air delivery section 1c and basic air delivery section 1b. The different air delivery sections are thus easily interchangeable via bayonet type joint 12, which utilizes lugs 13 to engage receptacles in the air delivery sections that lock the heating element and air delivery sections together.

Figure 7:
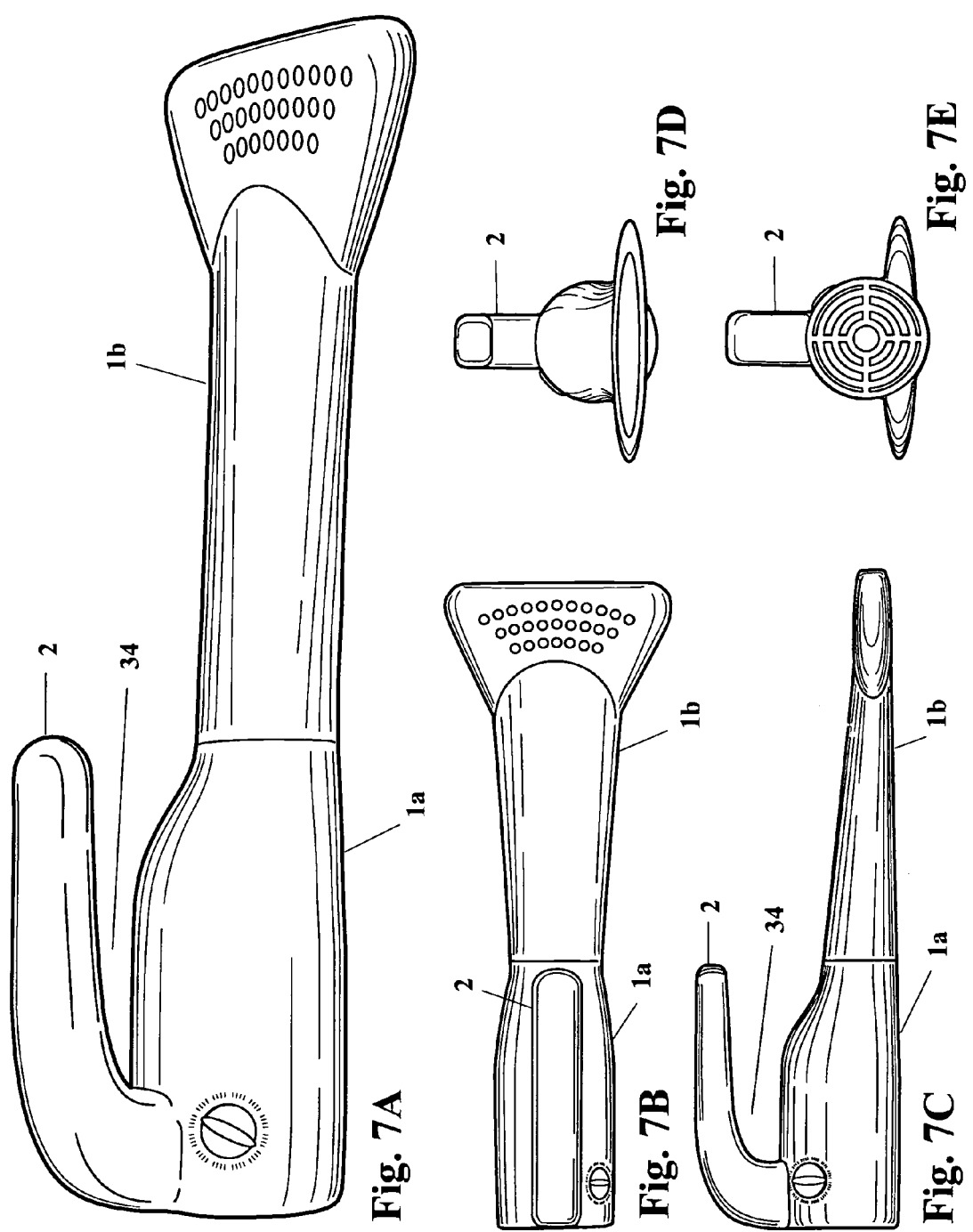
FIG. 7 is a three-dimensional (3D) rendering of the device of FIG. 1 showing a camera/perspective view in FIG. 7A, a top view in FIG. 7B, a side view in FIG. 7C, a front view in FIG. 7D and a back view in FIG. 7E.

Referring to FIG. 7, a 3D rendering of a preferred embodiment of the device of FIG. 1 is presented. This view shows a camera/perspective view in FIG. 7A, a top view in FIG. 7B, a side view in FIG. 7C, a front view in FIG. 7D and a back view in FIG. 7E. In FIG. 7C, air conditioning section 1a is shown to be U-shaped and to be adapted to receive the edge of a cover between its lower body portion 1a and its upper handle portion 2. In this configuration, the blanket is prevented from covering air intake 5 during operation of the device.

Figure 8:
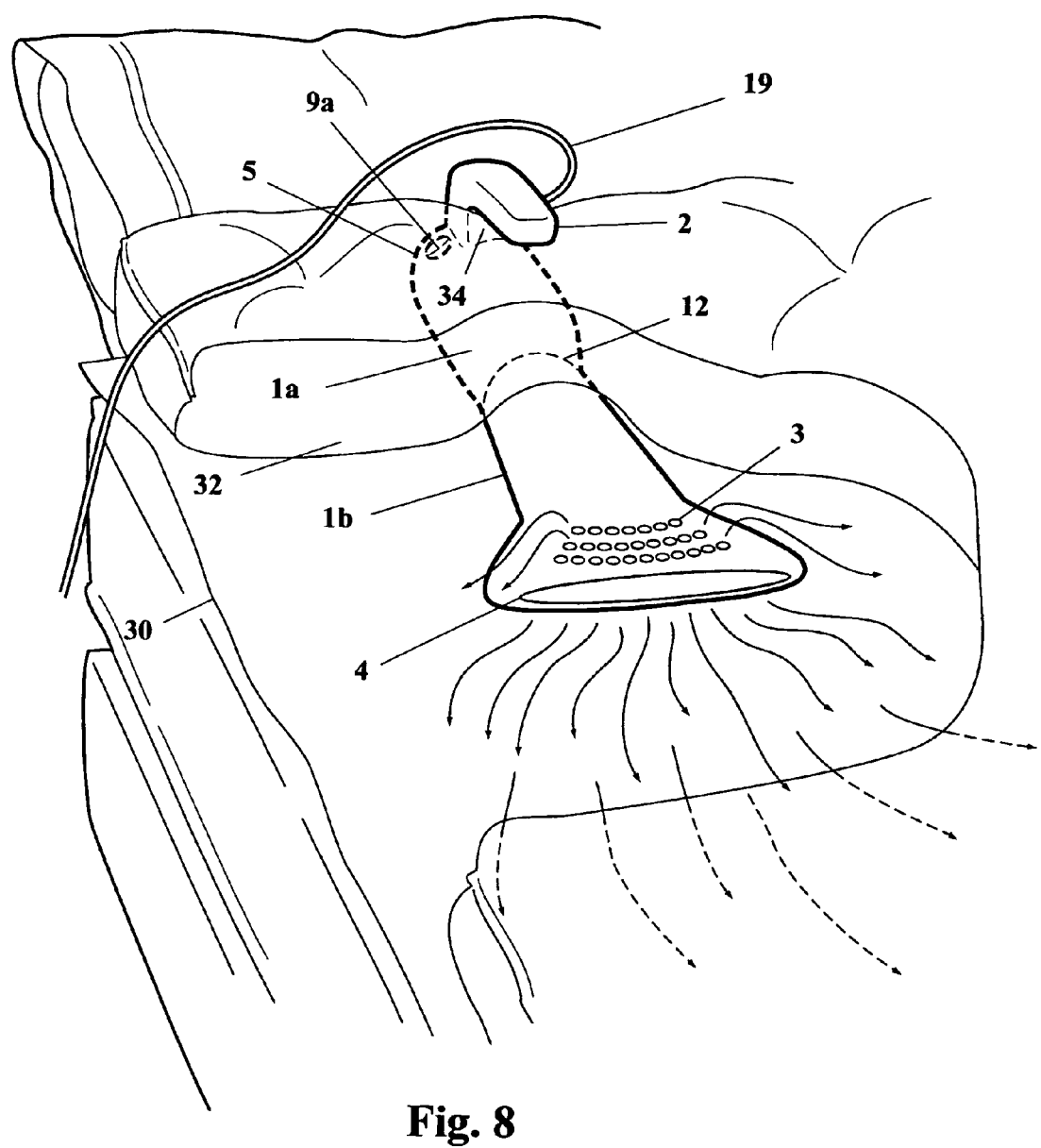
FIG. 8 is a 3D cut-away rendering of the device of FIG. 1 in use. In this view, the device is situated between the bed cover (which has a portion cut away for clarity) and the bottom sheet.

Referring to FIG. 8, a 3D view of the device in use is presented. In use, the device is plugged into an electrical receptacle and placed under the undisturbed covers or blankets on a bed, either from the front of the bed facing the foot, from the side, or from the foot facing forward. In this instance, the device is placed in a bed on top of bottom sheet 30 so that the edge of cover 32 fits in slot 34. The device is positioned such that the entire main body 1a and 1b of the device is under the covers or blankets 32, resting on top of the bottom sheet or bed linen 30, with the handle 2 on top of the covers or blankets 32. In this way, the handle acts not only as a means of easily manipulating and positioning the device, but also as a catch that helps to hold the unit in place and that prevents the covers from falling over rear air intake 5 and blocking the flow of air. The device is then activated and left to complete an automatic run cycle of 1 to 5 minutes by setting the timer dial 9a. If further heating or cooling is desired, timer dial 9a may be re-set such that the device re-activates and operates for additional cycles. Preferably, air delivery section 1b is sufficiently elongated that air discharged by the device inflates the bedding before escaping.

A preferred embodiment of heating element section 1a utilizes a heating coil to heat the air passing through it. This version is used during the cold months of the year for warming a bed. Another preferred embodiment of heating/cooling section 1aa contains thermoelectric module 15 that utilizes the Peltier effect to either heat or cool air passing through the device. It is used at any time during the seasonal cycles to either warm or cool a bed as desired. To this end, the heating/cooling embodiment of the invention can be easily switched from heating to cooling via polarity switch 21. Peltier effect elements are well known in the art as disclosed in U.S. Pat. No. 4,777,802, the disclosure of which patent is incorporated by reference as if fully set forth herein.

Either embodiment of the invention may be used interchangeably with different air delivery sections. FIG. 3 shows basic air delivery section 1b that is designed for general use that is suitable for a variety of beds. FIG. 2 shows thermal gel air delivery section 1d, which is designed as a thermal mass to absorb and retain the temperature of the air passing through the tortuous channels within it. After deactivation of the device, thermal gel air delivery section 1d may be detached and placed anywhere in the bed or against the resting body to provide additional passive radiant and direct contact heating or cooling.

FIG. 4 shows a child's version of an air delivery section created in the form of a stuffed toy dragon 1c. A variety of toy sections may be created using elongated creatures like snakes or alligators that will work in the same manner as the dragon toy depicted. The materials comprising the exterior of the toy air delivery section 1c are soft and flexible and able to be easily deformed. The interior is comprised of a length of semi-rigid heat resistant tubing that may slightly deform but not collapse. This tubing therefore maintains an unrestricted air channel that conducts the flow of air from the connection point to the primary air exit 4 and secondary air exits 3. The tubing is covered in a layer of thermal mass gel, allowing toy air delivery section 1c to retain heat or cold from the conditioned air that passes through it. After the bed has been initially warmed or cooled, child's stuffed toy air delivery section 1c can be detached from heating/cooling element section 1a and left with the child to cuddle with, providing an additional level of comfort as a further aid to sound sleep.

Figure 9:
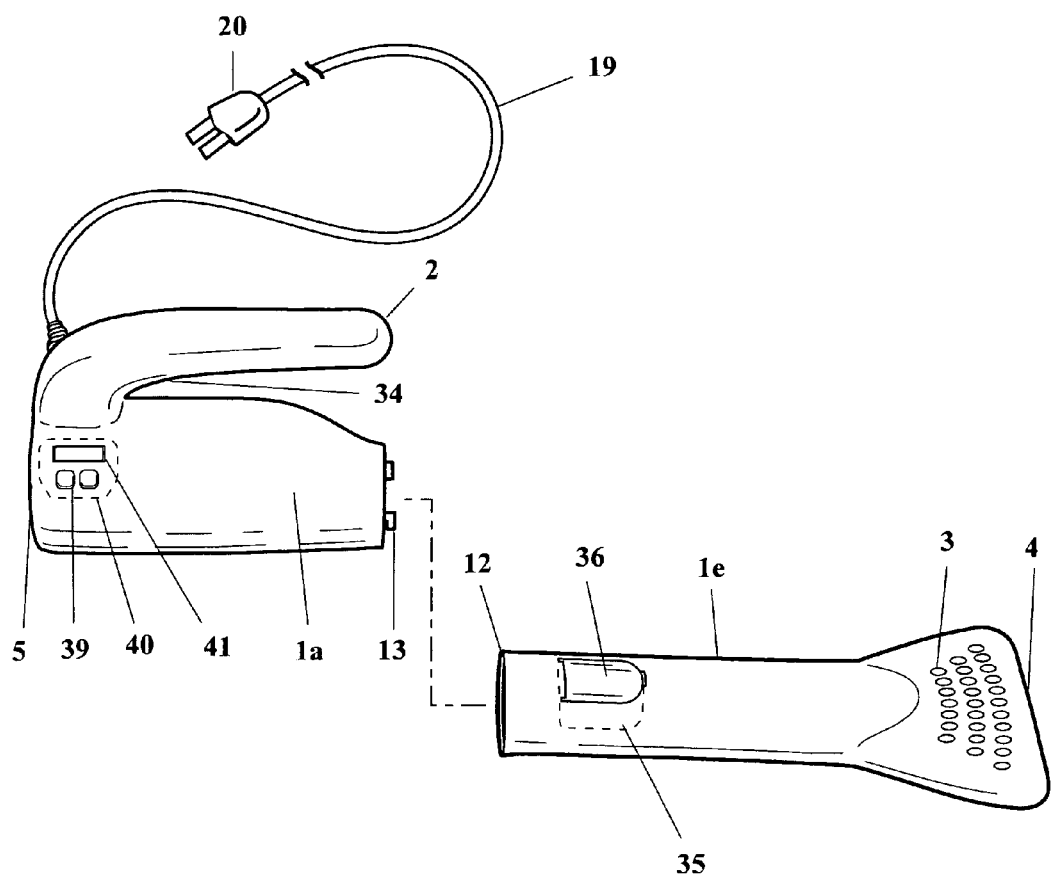
FIG. 9 is a right side perspective view of another preferred embodiment of the device, showing an exterior view of a heating element section with digital timer, pushbuttons and liquid crystal display (LCD) panel, separated from an herbal infuser air delivery section.

Referring to FIG. 9, a right side perspective view of another preferred embodiment of the device is presented. This figure shows an exterior view of heating element section 1a detached from herbal infuser air delivery section 1e. Herbal infuser enclosure door 36 is located on the top of the air delivery section and is shown in the closed position with the size and position of internal enclosure 35 indicated by dotted lines. Heating element section 1a is also shown with the size and position of digital timer unit 40 indicated by dotted lines. Exterior pushbuttons 39 are used for setting the activation time for the device and the number of minutes the device remains in operation. LCD panel 41 displays the activation time and associated numeric timer information.

Figure 10:
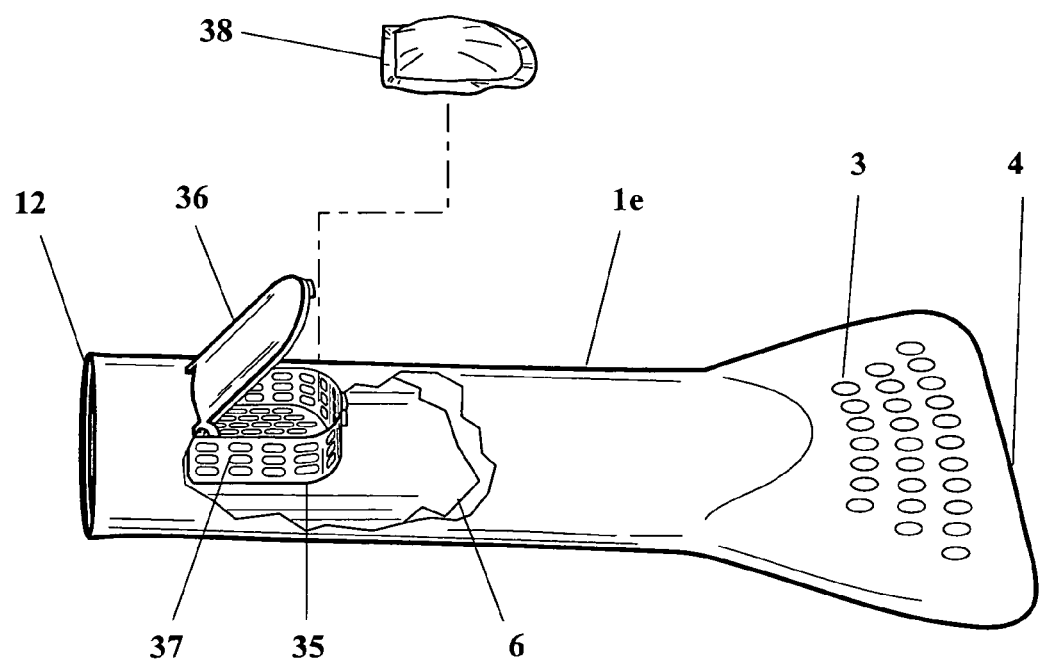
FIG. 10 is a right side perspective view of a preferred embodiment of the herbal infuser air delivery section, showing a cutaway view of the interior structure, displaying the perforated herbal infuser basket, the infuser enclosure cover in the open position and a shaped herbal packet that is insertable in the enclosure.

Referring to FIG. 10, a right side perspective view of herbal infuser air delivery section 1e is presented, showing a cutaway view of its interior structure wherein the perforated herbal infuser enclosure 35 is illustrated. Infuser enclosure cover 36 is shown in the open position, allowing shaped herbal packet 38 to be placed in the enclosure basket. Enclosure door 36 is then snapped closed and the device operated in the manner heretofore described. Heated air passing through herbal infuser air delivery section 1e passes over and warms herbal packet 38 by virtue of numerous enclosure perforations 37, thereby infusing the aromatic herbal scent and influence into the bed. Different varieties of aromatic herbal packets may thus be used and fresh packets easily installed as often as desired. Alternatively, aromatic packets that are not derived from herbs may be used. A person skilled in the art would understand that any aromatic substance may be held in the stream of warm air moving through the device and incorporated into that stream of warm air.

Many variations of the invention will occur to those skilled in the art. Some variations include heat/cold storage. Other variations call for a toy-shaped air delivery section. Still other variations call for an aromatic infuser air delivery section. All such variations are intended to be within the scope and spirit of the invention.

What is claimed is:

1. A device for modifying the temperature of bedding comprising a bed cover, said device comprising:
    a housing having an exterior and an interior, said housing defining an air intake, an air plenum and an air outlet;
    a fan mounted in said housing for moving air in said air intake, through said plenum and out said air outlet;
    a heat transfer element mounted within said housing for modifying the temperature of the air entering said air intake;
    a temperature sensor mounted in said plenum for sensing the temperature of the air moving through said plenum;
    a control circuit connected to said temperature sensor, said control circuit being operative to maintain the temperature of air moving through said plenum at or below a selected temperature;
    a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and
    an elongated air delivery section having two ends and defining an air entrance at one end, a primary air exit at the other end and a plurality of secondary air exits adjacent to the other end, said air entrance being adapted to connect to said air outlet;
    wherein said elongated air delivery section has a longitudinal axis and comprises a flattened portion;
    wherein said elongated air delivery section comprises means for suspending an aromatic element in and introducing an aromatic substance into the air moving through said elongated air delivery section such that said air is modified or further conditioned by said elements;
    wherein said primary air exit is situated at the terminus of said flattened portion and is adapted to discharge air substantially parallel to said longitudinal axis and far enough beneath a bed cover to cause the bedding to inflate; and
    wherein said plurality of secondary air exits are situated within said flattened portion and are adapted to discharge air substantially perpendicular to said longitudinal axis.

2. The device of claim 1 further comprising a handle attached to said housing.

3. The device of claim 2 wherein said handle is attached to the top rear of said housing and is forward projecting.

4. The device of claim 1 wherein said heat transfer device is a heating element.

5. The device of claim 1 further comprising a power cord for supplying power to the device.

6. The device of claim 1 further comprising a bayonet joint between said elongated air delivery section and said housing; and
    wherein said elongated air delivery section is attachable to and detachable from said housing by means of said bayonet joint.

7. The device of claim 1 wherein the selected amount of time is variable between about one minute and about five minutes.

8. A device for modifying the temperature of bedding, said bedding comprising a bottom sheet and a cover, said device comprising:
    an air conditioning section having an exterior and an interior having an insulating liner, said air conditioning section defining an air intake, an air plenum and an air outlet and having a U-shaped slot that is adapted to receive an edge of said cover;
    a fan mounted in said air conditioning section for moving air in said air intake, through said plenum and out said air outlet;
    a heat transfer element mounted within said air conditioning section for modifying the temperature of the air entering said air intake;
    a temperature sensor mounted on said heat transfer element for sensing its temperature;
    a control circuit connected to said temperature sensor, said control circuit being operative to maintain the temperature of the heat transfer element at or below a selected temperature;
    a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and
    an elongated air delivery section having two ends and defining an air entrance at one end, a primary air exit at the other end and a plurality of secondary air exits adjacent to the other end, said air entrance being adapted to connect to said air outlet.

9. A device for modifying the temperature of bedding, said bedding comprising a bottom sheet and a cover, said device comprising:
    an air conditioning section comprising a body portion and a handle portion, said an air conditioning section having an exterior surface that is adapted to receive an edge of said cover between said body portion and said handle portion and having an interior surface defining an air intake, an air plenum and an air outlet;

a fan mounted in said air conditioning section for moving air in said air intake, through said plenum and out said air outlet;

a heat transfer element mounted within said air conditioning section for modifying the temperature of the air entering said air intake;

a temperature sensor mounted on said heat transfer element for sensing its temperature;

a control circuit connected to said temperature sensor, said control circuit being operative to maintain the temperature of the heat transfer element at or below a selected temperature;

a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and an elongated air delivery section having two ends with an air entrance at one end and a primary air exit at the other end, said air entrance being adapted to connect to said air outlet.

10. A device for modifying a bedding environment, said bedding comprising a bottom sheet and a cover, said device comprising:

an air conditioning section comprising a body portion and a handle portion, said an air conditioning section having an exterior surface that is adapted to receive an edge of said cover between said body portion and said handle portion and having an interior surface defining an air intake, an air plenum and an air outlet;

a fan mounted in said air conditioning section for moving air in said air intake, through said plenum and out said air outlet;

a heat transfer element mounted within said air conditioning section for modifying the temperature of the air entering said air intake;

a temperature sensor mounted on said heat transfer element for sensing its temperature;

a control circuit connected to said temperature sensor, said control circuit being operative to maintain the temperature of the heat transfer element at or below a selected temperature;

a timer mounted within said housing, said timer being operative to activate said fan and heat transfer element either immediately or at any specified time within a twenty-four hour period upon being turned on or set by means of either a timer dial or a plurality of pushbuttons and a display panel and to deactivate said fan and heat transfer element after a selected amount of time; and an elongated air delivery section having two ends with an air entrance at one end and a primary air exit at the other end, said air entrance being adapted to connect to said air outlet;

wherein said elongated air delivery section comprises means for introducing an aromatic substance into the air moving through said elongated air delivery section such that said air is modified or further conditioned.

11. A method for modifying the temperature of bedding comprising a bottom sheet and a cover, said method comprising:

placing the device of claim 2 within the bedding with said handle on top of the cover and said outlet below the cover; and setting the timer to cause the device to operate, thereby inflating the bedding.

12. A method for modifying the temperature of bedding comprising a bottom sheet and a cover having an edge, said method comprising:

placing the device of claim 8 within the bedding with the edge of the cover being disposed in U-shaped slot and said outlet being disposed below the cover; and setting the timer to cause the device to operate.

13. A method for modifying the temperature of bedding comprising a bottom sheet and a cover, said method comprising:

a step for placing the device of claim 9 within the bedding with said handle portion on top of the cover and said outlet below the cover; and a step for setting the timer to cause the device to operate.

14. A method for modifying the environment of bedding, said bedding comprising a bottom sheet and a cover, said method comprising:

a step for placing the device of claim 10 within the bedding with said handle portion on top of the cover and said outlet below the cover; and a step for setting the timer to cause the device to operate.

* * * * *